United States Patent [19]
Albrecht et al.

[11] Patent Number: 5,821,198
[45] Date of Patent: Oct. 13, 1998

[54] LIQUID HERBICIDAL AGENTS

[75] Inventors: Konrad Albrecht; Rudolf Heinrich, both of Kelkheim; Hans Schumacher, Flörsheim am Main, all of Germany

[73] Assignee: Hoechst Aktiengesellschaft, Frankfurt, Germany

[21] Appl. No.: 455,664

[22] Filed: May 31, 1995

Related U.S. Application Data

[63] Continuation of Ser. No. 106,322, Aug. 13, 1993, abandoned, which is a continuation of Ser. No. 531,851, May 31, 1990, abandoned.

[30] Foreign Application Priority Data

Jun. 2, 1989 [DE] Germany .......................... 39 17 959.1

[51] Int. Cl.$^6$ ...................................................... A01N 9/00
[52] U.S. Cl. ........................................ 504/270; 71/DIG. 1
[58] Field of Search ........................... 504/270; 71/DIG. 1

[56] References Cited

U.S. PATENT DOCUMENTS

| | | | |
|---|---|---|---|
| 4,188,202 | 2/1980 | Gillings et al. | 71/88 |
| 4,589,908 | 5/1986 | Schumacher et al. | 71/88 |
| 4,626,274 | 12/1986 | Hausmann et al. | 71/93 |
| 4,793,850 | 12/1988 | Koester et al. | 71/79 |
| 4,888,041 | 12/1989 | Jackson et al. | 71/88 |
| 4,966,621 | 10/1990 | Heinrich et al. | 71/88 |

FOREIGN PATENT DOCUMENTS

| | | |
|---|---|---|
| 567595 | 11/1987 | Australia . |
| 597314 | 5/1990 | Australia . |
| 0 110 168 | 6/1985 | European Pat. Off. . |
| 0 144 796 | 6/1985 | European Pat. Off. . |
| 0 224 846 | 6/1987 | European Pat. Off. . |
| 3304677 A1 | 2/1983 | Germany . |
| 3033335 A1 | 9/1990 | Germany . |

*Primary Examiner*—Brian M. Burn
*Attorney, Agent, or Firm*—Frommer Lawrence & Haug LLP

[57] ABSTRACT

The present invention relates to liquid herbicidal agents in the form of emulsifiable concentrates (EC) or concentrated emulsions (EW), which, in addition to 1–40% by weight of the active compound diclofop-methyl (I), fenoxaprop-ethyl (II) or the optically active isomer (D+) thereof fenoxaprop-P-ethyl (III), contain, as surfactants, 0.5–30% by weight of ($C_{10}$–$C_{18}$)-fatty alcohol polyglycol ethers or ($C_8$–$C_9$)-alkylphenyl polyglycol ethers which are ethoxylated with 6–10 mol of ethylene oxide, and in the case of EC formulations 0.5–7% by weight of calcium ($C_8$–$C_{14}$)-alkylbenzenesulfonate, and in the case of EW formulations, as a dispersing agent, 0.5–7% by weight of an ethylene oxide-propylene oxide-ethylene oxide block copolymer phosphorylated in the alpha- and omega-position, or a salt thereof, in addition to the customary formulation constituents.

Compared with the known active compound formulations, these have significantly increased activities and improved mixing properties with water and other commercially available preparations containing active compounds.

11 Claims, No Drawings

LIQUID HERBICIDAL AGENTS

This application is a continuation of application Ser. No. 08/106,322, filed Aug. 13, 1993, (now abandoned) which is a continuation of application Ser. No. 07/531,851, filed May 31, 1990 (now abandoned).

The present invention relates to liquid herbicidal agents in the form of emulsifiable concentrates (EC) or concentrated emulsions (EW), which, in addition to 1–40% by weight of the active compound diclofop-methyl (I), fenoxaprop-ethyl (II) or the optically active isomer (D+) thereof fenoxaprop-P-ethyl (III), contain, as surfactants, 0.5–30% by weight of ($C_{10}$–$C_{18}$)-fatty alcohol polyglycol ethers or ($C_8$–$C_9$)-alkylphenyl polyglycol ethers which are ethoxylated with 6–10 mol of ethylene oxide, and in the case of EC formulations 0.5–7% by weight of calcium ($C_8$–$C_{14}$)-alkylbenzenesulfonate, and in the case of EW formulations, as a dispersing agent, 0.5–7% by weight of an ethylene oxide-propylene oxide-ethylene oxide block copolymer phosphorylated in the alpha- and omega-position, or a salt thereof, in addition to the customary formulation constituents.

The agents according to the invention can also contain, in addition to mixtures of the surfactants, mixtures of the active compounds I/II or I/III mentioned.

6–40% by weight of active compound, 1–20% by weight of the polyglycol ethers and in each case 1–5% by weight of calcium alkylbenzenesulfonate and/or phosphorylated block copolymers are preferred.

Examples which may be mentioned of the fatty alcohol polyglycol ethers are the ®Genapol X grades (HOECHST AG), in particular those of chain length $C_{10}$–$C_{14}$, especially isotridecanol polyglycol ether. By ($C_8$–$C_9$)-alkylphenyl polyglycol ethers there are to be understood, in particular, the ®Arkopal N grades (HOECHST AG).

Calcium alkylbenzenesulfonate furthermore preferably means that of chain length $C_{10}$–$C_{12}$, in particular calcium dodecylbenzenesulfonate.

Possible phosphorylated ethylene oxide-propylene oxide-ethylene oxide block copolymers to be used according to the invention are, in particular, those of the formula IV and salts thereof The compound I has excellent selective herbicidal actions against weeds in crop plants. The compounds II and III have an excellent action in the pre- and post-emergence method against a broad spectrum of harmful grasses, being tolerated by dicotyledonous crop plants as well as some cereal varieties and rice.

It is known that the activity of herbicides can in some cases be improved by mixing the active compounds with surface-active substances or oils or both. This is done, for example, with non-selective herbicides, such as paraquat, glyphosate or glufosinate (EP-A 0,048,436, 0,290,416 and 0,268,574). The discovery of additives which increase the action in selective herbicides is more difficult. Where substances which increase the action are found at all, the selective herbicides may, however, be given phytotoxic properties, i.e. they may lose their selectivity towards certain useful plants and thus also the advantages which these modern active compounds offer (cf. T. E. Whitmore in Farm Chemicals 2/1985, pages 18–21, and P. M. Neumann and K. Prinz in J. Sci. Fd. Agric. 1975 25, pages 221–226, and U.S. Pat. No. 4,084,956). According to U.S. Pat. No. 4,084,956, short-chain liquid surfactants cause barban to lose its selectivity, but it was possible to improve the action by solid, waxy surface-active substances, the selectivity being retained. If increases in action can be achieved by surfactants at all, specific substances evidently in each case respond specifically to certain active compounds. Thus it is known, for example, from DE-A 2,554,532 that the herbicidal action of methyl 3-(p-chlorophenyl)-2-chloropropionate can be improved only by a certain dodecylpolyglycol ether in the presence of paraffin oils. On the other hand, for example, it was not possible to increase the action of benzoylprop-ethyl by surfactants (Zeitschrift für Pflanzenkrankheiten und Pflanzenschutz, Hohenheim, Supplement VII (1975)). The tolerance of active surfactants for selective herbicides is in most cases influenced very greatly by the climate and soil, so that additives which increase the action can in most cases be used only in certain climate zones because of such risks.

It has now been found, surprisingly, that the herbicidal activity of the active compounds I–III can also be significantly improved under various climate conditions, their selectivity being retained, if these are employed in the form

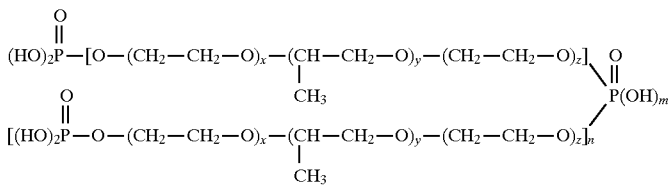

(IV)

in which x, y and z independently of one another are a number from 2 to 200 and m and n are 0, 1 or 2, where the sum n+m must be 2.

Preferably, x and y have the same meaning and are, in particular, a number from 30 to 100; y is, in particular, a number from 20 to 100, and n is, in particular, 0. These block polymers can be employed as mixtures. Their preparation is described in JA-A 7,247,982 or in DE-A 3,542,441.

Possible salts are, in particular, the alkali metal, alkaline earth metal, ammonium, mono-, di- or trialkylammonium or mono-, di- or trialkanolammonium salts. These have, in particular, 1 to 5 carbon atoms in the alkyl or alkanol part.

The compounds of the formulae I and II are known and are described in "The Pesticide Manual" 8th edition, British Crop Protection Council, 1987. The compound III can be prepared from II by known methods.

of the agents (formulations) according to the invention. These formulations can contain, in addition to the customary solvents (about 5–70% by weight), such as aromatic petroleum distillate (®Solvesso 150, ®Solvesso 200; Exxon Chem.), xylene, cyclohexanone, dimethylformamide, N-methylpyrrolidone, phthalic acid esters or mixtures thereof, about 2–15% by weight of the customary emulsifiers, such as castor oil ethoxylates, fatty amine ethoxylates and fatty alcohol polyglycol ethersulfonic acid salts, as an example of anionic surfactants, block polymers of polyoxyethylene and polyoxypropylene and corresponding block copolymers, and in the case of EW formulations about 5–40% by weight of water and about 0–15% by weight of antifreeze, such as glycerol, glycols (ethylene glycol, propylene glycol or monomethyl ethers thereof) or urea.

To stabilize the active compounds against hydrolysis or racemization in the case of III, the preparations can also contain stabilizers, such as epoxidized soya or linseed oil or aliphatic esters, and in the case of EWs also inorganic or organic acids or bases for the purpose of maintaining a certain pH.

The abovementioned formulation constituents are described, for example, in:

Watkins, "Handbook of Insecticide Dust Diluents and Carriers", 2nd edition, Darland Books, Caldwell N.J.; H. v. Olphen, "Introduction to Clay Colloid Chemistry", 2nd edition, J. Wiley & Sons, N.Y.; Marschen, "Solvents Guide", 2nd edition, Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte (Surface-active Ethylene Oxide Adducts)", Wiss. Verlagsgesell., Stuttgart 1976; and Winnacker-Küchler, "Chemische Technologie (Chemical Technology)", Volume 7, C. Hauser Verlag München, 4th edition 1986.

The EC and EW formulations according to the invention can be prepared in a manner which is known per se.

EC: The active compound or compounds are dissolved in the solvents described (if appropriate with addition of the emulsifiers mentioned) and the wetting agents according to the invention, calcium alkylbenzenesulfonate and the remaining formulation constituents are added, while stirring intensively (cf. Table 1).

EW: The active compound solution (if appropriate with emulsifier) and the wetting agents described are intimately mixed, and this mixture is stirred into an aqueous phase which contains the block polymers according to the invention. The remaining constituents are then added (cf. Table 1 and EP-A 224,846 and 118,759).

Compositions of EC and EW formulations of the active substances I, II and III are listed in Table 1. Formulations No. 2, 5, 7, 8, 12 and 15 were prepared by customary methods, and formulations 1, 3, 4, 6, 9, 10, 11, 13, 14 and 16 are formulations according to the invention.

The surprisingly large improvement in the herbicidal activity of the formulations claimed can be seen from the results of Table 2. The results were confirmed in experiments carried out repeatedly in different climatic zones such as Europe, Canada and Brazil. It is completely surprising here that, in spite of the relatively high contents of additives, the formulations claimed cause no damage in the crop plants to be protected, for example to wheat, beet and soya bean. The amount of active compound applied/ha can in this way be effectively reduced, which makes the plant protection agent less expensive and leads to less environmental pollution.

The application costs can be reduced and additional applications can be spared if it is possible to discover formulations of the compounds I, II and III which form such stable aqueous emulsions that further plant protection agents, for example fungicides for the simultaneous control of fungal attack, or herbicides for the purpose of extending the biological activity or fertilizers, can also be mixed into these. The farmer can then achieve several aims with one spraying. However, the emulsions very often "break" when further plant protection agents or fertilizers are admixed. The emulsions "oil" out, i.e. the droplets of the plant protection formulations emulsified in water agglomerate to coarse drops, which then separate and lead to phase separation. During admixing of wettable powders, flocculation very often additionally occurs, as does agglomeration of the solid active compound particles of the admixed preparation, which are fine in these cases and which preferentially also include large amounts of the emulsified active compounds. Such spray liquors are then unusable, since uniform distribution of the active compound on spraying is not guaranteed. The consequence would be reduced actions on the one hand and at the same time damage by excessive concentrations of the active compound on the other hand.

The abovementioned advantages can be realized easily on the basis of the significantly improved mixing properties of the agents according to the invention with commercially available active compound formulations (cf. Table 3). The agent concentrations stated correspond to customary field practice. For the miscibility testing, the spray liquors remained in measuring cylinders at 20°–22° C. for 6 hours without vibration.

The formulations claimed are moreover distinguished by a very good miscibility with water, even at very high use concentrations (cf. Table 4). This increased miscibility in comparison with known formulations allows the agents according to the invention already to be applied with very low amounts of spray liquor/ha. In this way, only water application amounts of 20–60 l/ha are required, for example, to prepare the finished spray liquors. Very large areas can in this way be treated with one spraying. This is particularly important for application from an aeroplane.

Before the application, the agents according to the invention are diluted with water to the particular use concentration desired. The water application amounts vary within a wide range, depending on the indication and technical equipment. The water application amount/ha is in general about 20–600 l, usually 200–400 l.

Summarizing, this means that the agents according to the invention are distinguished by increased activity of the active compounds, their selectivity being retained, significantly improved mixing properties with known active compound formulations and water and increased stability and storage life compared with the prior art.

TABLE 1

COMPOSITIONS OF DICLOFOP-METHYL AND FENOXAPROP-ETHYL EC AND EW FORMULATIONS IN % BY WEIGHT

| Formulation constituents | Formulation No. | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Diclofop-methyl (I) | 19.0 | 28.4 | 28.4 | 28.4 | 33.6 | 36.0 | 36.0 | | | | | | | | | |
| Fenoxaprop-ethyl (II) | | | | | | | | 10.0 | 10.0 | 12.5 | 6.0 | | | | | |
| Fenoxaprop-P-ethyl (III) | | | | | | | | | | | | 9.5 | 12.0 | 6.0 | 7.5 | 7.5 |
| Safener Hoe 70542 (Hoechst AG) | | | | | | | | | | | | | | | 2.0 | 2.0 |
| Xylene | 59.5 | | | | | 41.3 | 42.0 | 46.0 | 36.7 | 39.0 | | 55 | 39.5 | | | |
| Solvesso 150 | | | 41.6 | 26.6 | 24.6 | | | | | | | | | | | |

TABLE 1-continued

COMPOSITIONS OF DICLOFOP-METHYL AND FENOXAPROP-ETHYL EC AND EW FORMULATIONS IN % BY WEIGHT

| Formulation constituents | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Solvesso 200 | | | | | 20.0 | | | | | | 23.0 | | | 20.0 | 40.0 | 40.0 |
| Dimethylformamide | | | | | | | | | | 25.0 | | 25.0 | 14.0 | | | |
| Diethyl phthalate | | | | | | | | | | | 20.0 | | | 20.0 | | |
| Cyclohexanone | | 20.0 | 20.0 | 20.0 | | 10.0 | 10.0 | 35.0 | 30.0 | | | | | | | |
| Propylene glycol monomethyl ether | | | | | 10.0 | | | | | | | | | | | |
| Propylene glycol | | | | | | | | | | | | | | 6.0 | | |
| Glycerol | | | | | | | | | | | 8.0 | | | | 8.0 | 8.0 |
| Ca dodecylbenzenesulfonate 70% strength solution in isobutanol | 3.5 | 4.0 | 4.0 | 5.0 | | 4.2 | 4.5 | 3.0 | 3.8 | 2.0 | | 4.0 | 4.0 | | | |
| Castor oil + 40 mol of ethylene oxide | | 6.0 | 6.0 | 6.0 | 9.0 | 6.5 | 6.5 | 6.0 | 6.5 | 6.0 | 4.0 | 6.5 | 6.5 | | 2.0 | 2.0 |
| Castor oil + 36 mol of ethylene oxide | 3.0 | | | | | | | | | | | | | | | |
| Oleyl alcohol + 8 mol of ethylene oxide | | | | | | | 1.0 | | 1.0 | | | | | | | |
| Isotridecanol + 6 mol of ethylene oxide | 15.0 | | 15.0 | | | | | | | 12.0 | 7.5 | | | 12.0 | | 15.0 |
| Isotridecanol + 8 mol of ethylene oxide | | | | 15.0 | | | | | | | | | | | | |
| Monylphenol + 10 mol of ethylene oxide | | | | 1.0 | | 2.0 | | | | | 15.5 | | | | | |
| Octylphenol + 6.8 mol of ethylene oxide | | | | | | | | | | | | | 24.0 | | | |
| Phosphorylated ethylene oxide-propylene oxide-ethylene oxide block copolymer | | | | | 2.0 | | | | | | 3.0 | | | 4.0 | 2.3 | 2.2 |
| Sodium hydroxide solution (10% strength) | | | | | 0.4 | | | | | | 0.6 | | | 1.1 | 0.4 | 0.4 |
| Water | | | | | 25.0 | | | | | | 27.9 | | | 26.9 | 37.8 | 22.8 |
| Epoxidized soya oil | | | | | | | | | | | | | | 4.0 | | |

TABLE 2

Activity and tolerance of various formulations (Table 1) of diclofop-methyl and fenoxaprop-ethyl *)

| Active compound | Formulation No. | Dosage g of active compound/ha | Avena[1] sp. | Setaria[2] sp. | Lolium[3] sp. | Tritic.[4] aestivum | Beta[5] vulgaris | Glycine[6] max. |
|---|---|---|---|---|---|---|---|---|
| Diclofop-methyl | 2 | 540 | 65 | 70 | 80 | | | |
| Diclofop-methyl | 2 | 720 | 78 | 82 | 100 | 0 | 0 | 0 |
| Diclofop-methyl | 3 | 540 | 85 | 95 | 100 | 0 | 0 | 0 |
| Diclofop-methyl | 3 | 720 | 98 | 100 | 100 | 0 | 0 | 0 |
| Fenoxaprop-ethyl | 8 | 60 | 45 | 65 | — | 0 | 0 | 0 |
| Fenoxaprop-ethyl | 8 | 90 | 60 | 90 | — | 0 | 0 | 0 |
| Fenoxaprop-ethyl | 9 | 60 | 58 | 90 | — | 0 | 0 | 0 |
| Fenoxaprop-ethyl | 9 | 90 | 85 | 100 | — | 0 | 0 | 0 |
| Fenoxaprop-ethyl | 10 | 60 | 55 | 85 | — | 0 | 0 | 0 |
| Fenoxaprop-ethyl | 10 | 90 | 80 | 100 | — | 0 | 0 | 0 |
| Fenoxaprop-ethyl | 11 | 60 | 65 | 100 | — | 0 | 0 | 0 |
| Fenoxaprop-P-ethyl | 12 | 30 | 40 | 70 | — | 0 | 0 | 0 |
| Fenoxaprop-P-ethyl | 13 | 30 | 60 | 100 | — | 0 | 0 | 0 |
| Fenoxaprop-P-ethyl | 14 | 30 | 67 | 100 | — | 0 | 0 | 0 |

*) Mean values from field experiments carried out in Europe, Canada and Brazil
Use in 300 l of water after emergence of the plants
[1] Wild oats
[2] Millet varieties
[3] Common rye grass
[4] Wheat
[5] Beet
[6] Soya beans

TABLE 3

Example of miscibility tests on conventional formulations and the formulations claimed

| Experiment No. | Formulation No. | Use concentration | Mixing partner | Use concentration | Findings in the spray liquor after standing: |
|---|---|---|---|---|---|
| 1 | 2 | 2% | AUS solution [1] | 35% | 2% by volume oil on top. phase separation |
| 2 | 3 | 2% | AUS solution | 35% | homogeneous emulsion |
| 3 | 8 | 5% | Derosal 60 WP [2] | 5% | 35% by volume flaky, somewhat oily, loose sediment |
| 4 | 9 | 5% | Derosal 60 WP | 5% | only 5% by volume sediment[4] emulsion otherwise stable |
| 5 | 16 | 5% | Derosal 60 WP | 5% | only 5% by volume sediment[4] emulsion otherwise stable |
| 6 | 15 | 5% | Copper oxychloride 35 WP [3] | 6.6% | 16% by volume flaky and oily sediment |
| 7 | 16 | 5% | Copper oxychloride 35 WP | 6.6% | 2% by volume[4], normal sediment as with WP without addition of formulation 16. Emulsion otherwise homogeneous |

1) Ammonium nitrate-urea fertilizer solution consisting of 40% by weight of ammonium nitrate, 20% by weight of urea and 40% by weight of water
2) Wettable powder containing 60% by weight of the fungicide carbendazim (Derosal 60 ®)
3) Wettable powder containing 35% by weight of copper oxychloride (Haftvitigran ®)
4) Wettable powder suspensions almost always give sediments on standing. In the CIPAC test conditions, however, at least 50% of the active compound particles must remain in the suspension.
In experiments 3 and 6 the sediments are too high and moreover also have entrained portions of the active compound of compounds I, II and III present in the emulsion.

TABLE 4

Examples of the stability of emulsions of the EC and EW formulations claimed and customary EC and EW formulations at various use concentrations with standing times of 6 and 24 hours in water of 324 ppm calcium carbonate hardness at 20–22° C.

| Use concentrations (%) | 10 | | 20 | | 30 | | 40 | |
|---|---|---|---|---|---|---|---|---|
| Standing time of the emulsions (hours) | 6 | 24 | 6 | 24 | 6 | 24 | 6 | 24 |
| Product formulation (Table 1) No.: | | | | | | | | |
| 6 | + | + | + | + | + | + | + | + |
| 7 | + | + | + | + | 2 cr*) | 5 cr*) | 12 cr*) | 52 cr*) |
| 9 | + | + | + | + | + | + | 1 cr | 2 cr |
| 8 | + | + | + | 10 cr | 90 cr/o | 80 cr/o | 90 cr/o | 60 cr/o |
| 16 | + | + | + | + | + | + | + | + |
| 15 | 5 cr | 9 cr | 15 cr | 15 cr/o | 35 cr/o | 30 cr/o | 50 cr | 40 cr/o |
| 13 | + | + | + | + | + | + | + | + | cr = creamy sediment
cr/o = creamy-oily sediment (sometimes complete separation into visible oil, i.e. to the solution containing the active compound, which occasionally leads to a decrease in volume of the precipitate)
*) = figures in the table show % by volume of the phase which has separated out at the bottom
+ = homogeneous emulsion

We claim:

1. A herbicidal agent in the form of an emulsifiable concentrate (EC) which, in addition to 1–40% by weight of the active compound diclofop-methyl (I), fenoxaprop-ethyl (II) or the optically active isomer (D+) thereof fenoxaprop-P-ethyl (III), comprises as surfactants, 0.5–30% by weight of $C_{10}$–$C_{14}$ fatty alcohol polyglycol ethers or ($C_8$–$C_9$)-alkylphenyl polyglycol ethers which are ethoxylated with 6–10 mol of ethylene oxide, and 0.5–7% by weight of calcium ($C_8$–$C_{14}$)-alkylbenzenesulfonate, which further comprise solvents selected from the group consisting of aromatic petroleum distillates, xylene, cyclohexanone, dimethylformamide, N-methylpyrrolidine, phthalic acid esters and mixtures thereof, and which agent does not contain herbicidal ingredients in addition to the active compounds I, II and III, and wherein a combination of fenoxaprop-ethyl or fenoxaprop-P-ethyl with diclofop-methyl, and the surfactants alkylphenyl-polyglycol ether and calcium dodecylbenzene sulfonate are excluded.

2. An agent as claimed in claim 1, which contains ($C_{10}$–$C_{14}$)-fatty alcohol polyglycol ethers ethoxylated with 6–10 mol of ethylene oxide as surfactants.

3. An agent as claimed in claim 1, which contains isotridecanol polyglycol ether ethoxylated with 6–10 mol of ethylene oxide as the surfactant.

4. A herbicidal agent as claimed in claim 1 which further comprises 5–70% by weight of aromatic petroleum distillate, xylene, cyclohexanone, dimethylformamide, N-methylpyrrolidone, phthalic acid esters or mixtures thereof, as a solvent, and 2–15% by weight of castor oil ethoxylates, fatty amine ethoxylases and fatty alcohol polyglycol ethersulfonic acid salts, as an emulsifier.

5. An agent as claimed in claim 1, which, contains calcium ($C_{10}$–$C_{12}$) alkylbenzenesulfonate.

6. An agent as claimed in claim 1, which, in the case of an EC formulation, contains calcium dodecylbenzenesulfonate.

7. The herbicidal agent as claimed in claim 1 which contains 6 to 40% by weight of an active ingredient of formula (I), (II) or (III) or a mixture thereof, 1 to 20% by weight of polyglycol ethers, and 1 to 5% by weight of the calcium alkylbenzenesulfonate.

8. The herbicidal agent as claimed in claim 1 which contains 5 to 70% by weight of an organic solvent selected from the group consisting of aromatic petroleum distillate, xylene, cyclohexanone, dimethylformamide, N-methylpyrrolidon, phthalic acid esters and mixtures thereof.

9. The herbicidal agent as claimed in claim 1 which contains 2 to 15% by weight of an emulsifier selected from the group consisting of castor oil ethoxylates, fatty amine ethoxylates, polyglycol ethersulfonic acid salts and block polymers of polyethylene and polypropylene and corresponding phosphorylated black copolymers.

10. The herbicidal agent as claimed in claim 1 which contains 6 to 40% by weight of an active ingredient of formula (I), (II) or (III), 1 to 20% by weight of polyglycol ethers, 1 to 5% by weight of calcium alkylbenzenesulfonate, 5 to 70% by weight of an organic solvent selected from the group consisting of aromatic petroleum distillate, xylene, cyclohexanone, dimethylformamide and mixtures thereof, and 2 to 15% by weight of a castor oil ethoxylate.

11. The composition as claimed in claim 1, wherein the surfactant is isotridecanol, nonylphenol or octylphenol polyglycol ethers which are ethoxylated with 6–10 mol of ethylene oxide.

* * * * *